(12) United States Patent
Tateishi et al.

(10) Patent No.: US 11,486,892 B2
(45) Date of Patent: Nov. 1, 2022

(54) FLUID MEASURING DEVICE

(71) Applicants: PIONEER CORPORATION, Tokyo (JP); NIKKISO COMPANY LIMITED, Tokyo (JP)

(72) Inventors: Kiyoshi Tateishi, Kawagoe (JP); Wataru Onodera, Kawagoe (JP); Atsuya Ito, Kawagoe (JP); Tomoya Murakami, Makinohara (JP); Akari Agata, Makinohara (JP); Genki Adachi, Makinohara (JP)

(73) Assignees: AIR WATER BIODESIGN INC., Hyogo (JP); NIKKISO COMPANY LIMITED, Tokyo (JP)

( * ) Notice: Subject to any disclaimer, the term of this patent is extended or adjusted under 35 U.S.C. 154(b) by 528 days.

(21) Appl. No.: 16/345,065

(22) PCT Filed: Oct. 25, 2016

(86) PCT No.: PCT/JP2016/081625
§ 371 (c)(1),
(2) Date: Apr. 25, 2019

(87) PCT Pub. No.: WO2018/078728
PCT Pub. Date: May 3, 2018

(65) Prior Publication Data
US 2019/0277875 A1    Sep. 12, 2019

(51) Int. Cl.
*G01P 5/26* (2006.01)
*G01P 13/00* (2006.01)
(Continued)

(52) U.S. Cl.
CPC ............ *G01P 5/26* (2013.01); *G01F 1/00* (2013.01); *G01F 1/66* (2013.01); *G01P 13/0006* (2013.01)

(58) Field of Classification Search
CPC ......... G01P 5/26; G01P 13/0006; G01F 1/00; G01F 1/66
See application file for complete search history.

(56) References Cited

U.S. PATENT DOCUMENTS 5,587,785 A    12/1996 Kato et al.
5,982,478 A  * 11/1999 Ainsworth .............. G01P 5/001
                                                            356/28

(Continued)

FOREIGN PATENT DOCUMENTS

CN    102356297 A    2/2012
EP      2409115 A2   1/2012
(Continued)

OTHER PUBLICATIONS

Extended European Search Report issued in European Patent Application No. 16920227.2 dated May 15, 2020.
(Continued)

*Primary Examiner* — Elias Desta
(74) *Attorney, Agent, or Firm* — Nixon & Vanderhye

(57) ABSTRACT

This fluid measuring device is provided with: an irradiation unit that irradiates a fluid with light; a light receiving unit that receives light scattered by the fluid; a detecting unit that detects a backflow of the fluid on the basis of a light reception signal from the light receiving unit; and a calculating unit that calculates, on the basis of the detection result by the detection unit and the light reception signal from the light receiving unit, estimated fluid information indicating the flow rate or flow speed of the fluid. Accordingly, even when a backflow of the fluid temporarily occurs, the flow speed of the fluid can be precisely measured.

11 Claims, 14 Drawing Sheets

(51) Int. Cl.
　　*G01F 1/66*　　　(2022.01)
　　*G01F 1/00*　　　(2022.01)

(56) References Cited

U.S. PATENT DOCUMENTS

| | | | |
|---|---|---|---|
| 6,354,147 B1 * | 3/2002 | Gysling | G01N 29/42 |
| | | | 73/61.79 |
| 7,152,003 B2 * | 12/2006 | Loose | G01F 1/666 |
| | | | 702/45 |
| 9,383,235 B2 * | 7/2016 | Tokhtuev | G01F 1/06 |
| 2010/0276367 A1 | 11/2010 | Zhang | |
| 2012/0002189 A1 | 1/2012 | Bengoechea Apezteguia et al. | |
| 2012/0323502 A1 | 12/2012 | Tanoura et al. | |

FOREIGN PATENT DOCUMENTS

| | | |
|---|---|---|
| EP | 3045876 A1 | 7/2016 |
| JP | H07-311215 A | 11/1995 |
| JP | 2007-212271 A | 8/2007 |
| JP | 2012-521003 A | 9/2012 |
| JP | 5586476 B2 | 9/2014 |
| KR | 10-2011-0133609 A | 12/2011 |
| WO | 2010/106483 A2 | 9/2010 |
| WO | 2013/140583 A1 | 9/2013 |
| WO | 2015/033469 A1 | 3/2015 |
| WO | 2015/198470 A1 | 12/2015 |
| WO | 2016/046905 A1 | 3/2016 |

OTHER PUBLICATIONS

Kilpatrick, D. et al., "Fibre Optic Laser Doppler Measurement of Intravascular Velocity," Selected Papers on Optical Fibres in Medicine, Jan. 1, 1990, pp. 253-262.

International Search Report, dated Jan. 24, 2017, from corresponding PCT application No. PCT/JP2016/081625.

* cited by examiner

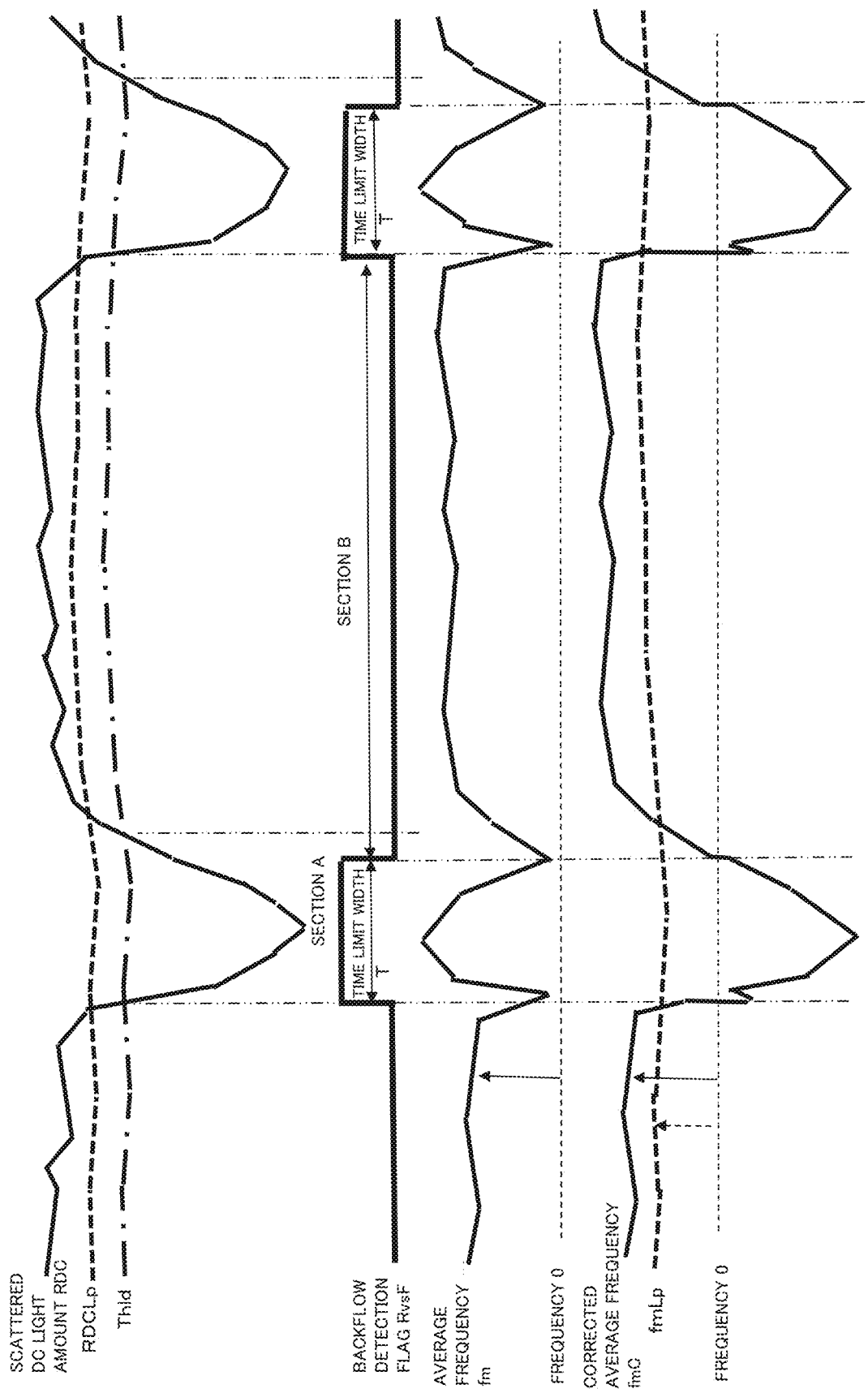

FLUID MEASURING DEVICE

TECHNICAL FIELD

The present invention relates to a fluid measuring apparatus configured to measure information about a fluid by irradiating the fluid with light.

BACKGROUND ART

For this type of apparatus, there is known an apparatus configured to irradiate a fluid with light and to receive scattered light, thereby measuring a fluid concentration, a flow volume, a flow velocity, and the like. For example, Patent Literature 1 discloses a technology/technique in which a blood flowing in an artificial dialysis apparatus is irradiated with light to measure a blood concentration (or a hematocrit value) and a blood flow volume.

CITATION LIST

Patent Literature

Patent Literature 1: Japanese Patent No. 5586476

SUMMARY OF INVENTION

Technical Problem

In the artificial dialysis apparatus, a blood collected from a patient flows in a tube by a power of a pump; however, the blood may temporarily flow backward in the tube because of characteristics of the pump. As a result, the measurement using the light may not be accurately performed.

In the aforementioned Patent Literature 1, there is no description about a backflow of the blood. Thus, if the backflow of the blood occurs, the blood concentration and the blood flow volume cannot be accurately measured, which is technically problematic.

The above is an example of problems to be solved by the present invention. It is therefore an object of the present invention to provide a fluid measuring apparatus configured to accurately measure information about a fluid.

Solution to Problem

The above object of the present invention can be achieved by a first fluid measuring apparatus provided with: an irradiating device configured to irradiate a fluid with light; a light receiving device configured to receive light scattered by the fluid; a detecting device configured to detect a backflow of the fluid on the basis of a received light signal of the light receiving device; and a calculating device configured to calculate estimated fluid information indicating a flow volume or a flow velocity of the fluid, on the basis of a detection result of the detecting device and the received light signal of the light receiving device.

The above object of the present invention can be achieved by a second fluid measuring apparatus provided with: an irradiating device configured to irradiate a fluid with light; a light receiving device configured to receive light scattered by the fluid; a detecting device configured to detect that a change amount of received light intensity indicated by a received light signal of the light receiving device is greater than or equal to a predetermined value; and a calculating device configured to calculate estimated fluid information indicating a flow volume or a flow velocity of the fluid, on the basis of a detection result of the detecting device and the received light signal of the light receiving device.

BRIEF DESCRIPTION OF DRAWINGS

FIG. 14 is a graph illustrating a method of limiting a time width regarding the detection of the backflow.

DESCRIPTION OF EMBODIMENTS

<1>

Figure 1:
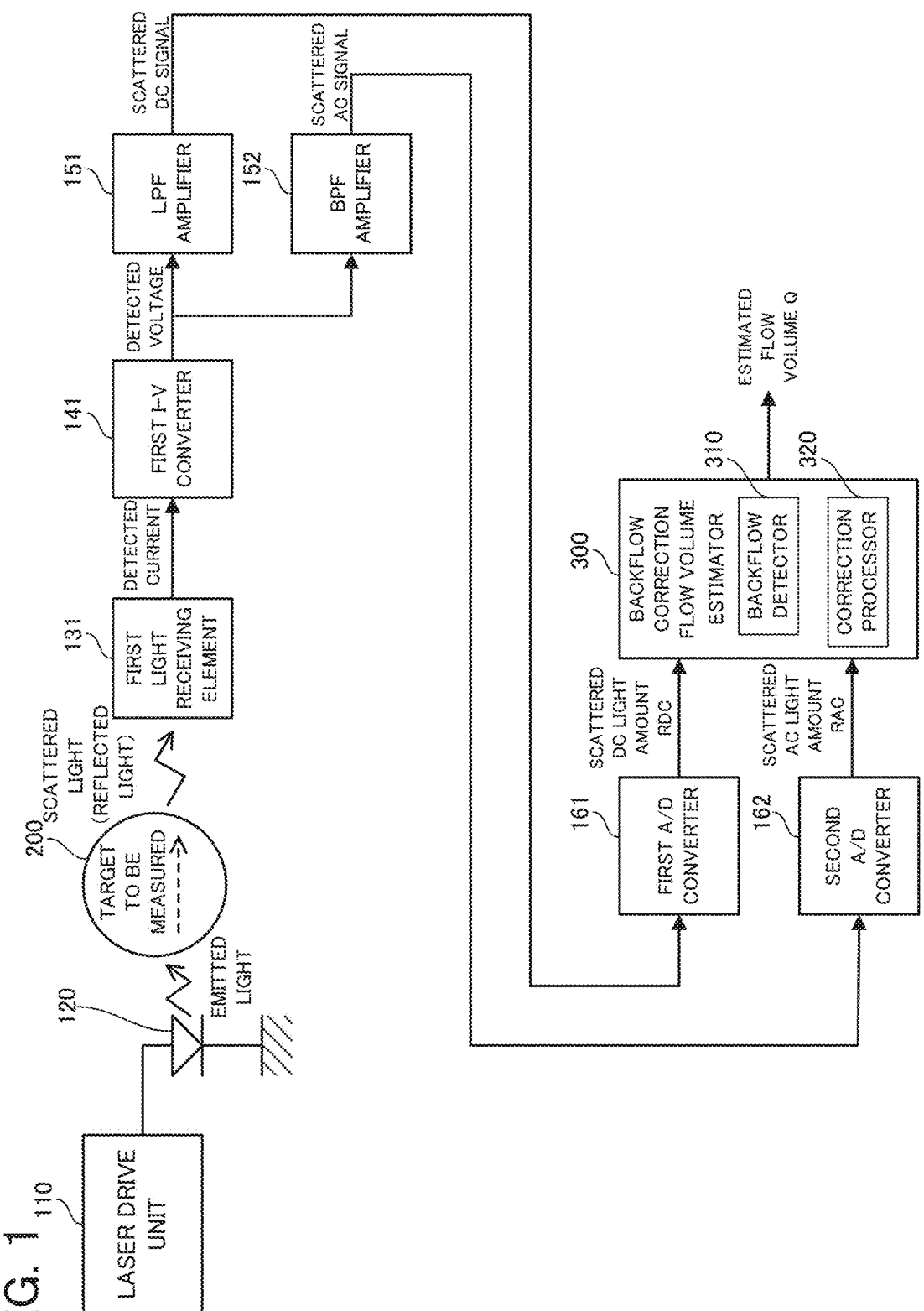
FIG. 1 is a schematic diagram illustrating an entire configuration of a fluid measuring apparatus according to a first practical example.

A first fluid measuring apparatus according to an embodiment is provided with: an irradiating device configured to irradiate a fluid with light; a light receiving device configured to receive light scattered by the fluid; a detecting device configured to detect a backflow of the fluid on the basis of a received light signal of the light receiving device; and a calculating device configured to calculate estimated fluid information indicating a flow volume or a flow velocity of the fluid, on the basis of a detection result of the detecting device and the received light signal of the light receiving device.

In operation of the first fluid measuring apparatus according to the embodiment, the light is applied to the fluid from the irradiating device. The applied light is, for example, laser light, and the light is applied by using a Fabry-Perot (FP) laser light source and a distributed feedback laser light source. Moreover, a specific example of the fluid is a blood or the like. Anything that flows and can be irradiated with the light from the irradiating device could be a measurement target.

The light applied from the irradiating device is scattered (i.e., transmitted or reflected) in the fluid, and is then received on the light receiving device. The light receiving device is configured to be, for example, a photo diode, and is configured to detect the intensity of the light, and to output the received light signal (i.e., the signal indicating the intensity of the received light).

The intensity of the light scattered in the fluid varies depending on a state of the fluid. It is thus possible to measure the information about the fluid (e.g., the flow volume or the flow velocity, etc.) by using the information owned by the light received on the light receiving device.

Particularly in the embodiment, the backflow of the fluid can be detected on the detecting device. The "backflow" herein may mean that the fluid flows in a different direction from the original, which may include a temporal flow or a partial flow. The detecting device is configured to detect the backflow of the fluid on the basis of the received light signal outputted from the light receiving device.

The detection result regarding the backflow of the fluid is used to calculate the estimated fluid information indicating the flow volume or the flow velocity of the fluid, together with the received light signal outputted from the light receiving device. The calculating device configured to calculate the estimated fluid information is configured to estimate the flow volume or the flow velocity of the fluid, for example, on the basis of whether or not the backflow occurs in the fluid, and on the basis of a power spectrum of the light indicated by the received light signal.

Here, if the information about the backflow of the fluid is not detected, it is hard to accurately calculate the estimated fluid information. According to studies by the present inventors, it has been found that the intensity of the scattered light from the fluid changes, temporarily significantly, if the backflow occurs in the fluid. Thus, if the flow volume or the flow velocity of the fluid is estimated only on the basis of the received light signal, the flow volume or the flow velocity may be erroneously estimated when the backflow occurs.

In the embodiment, however, as described above, the estimated fluid information is calculated on the basis of the detection result of the detecting device and the received light signal of the light receiving device. In other words, the flow volume or the flow velocity of the fluid is estimated in view of the occurrence of the backflow. Therefore, according to the fluid measuring apparatus in the embodiment, it is possible to accurately estimate the flow volume or the flow velocity of the fluid.

<2>

In one aspect of the fluid measuring apparatus according to the embodiment, the detecting device is configured to detect the backflow of the fluid if a change amount of received light intensity indicated by the received light signal is greater than or equal to a predetermined value.

According to this aspect, it is possible to detect the backflow of the fluid by comparing the change amount of the received light intensity with the predetermined value. The "predetermined value" may be a value set in accordance with the change amount of the received light intensity when the fluid flows backward, and may be obtained and set in advance, theoretically, experimentally, or experientially.

<3>

In another aspect of the fluid measuring apparatus according to the embodiment, the fluid measuring apparatus is further provided with an analyzing device configured to output an average frequency signal on the basis of the received light signal, wherein the calculating device is configured (i) to calculate the estimated fluid information on the basis of the average frequency signal in a period other than a backflow period in which the backflow of the fluid is detected, and (ii) to calculate the estimated fluid information on the basis of a corrected average frequency signal obtained by correcting the average frequency signal in the backflow period.

According to this aspect, in the period other than the backflow period, the estimated fluid information is calculated on the basis of the average frequency signal. In the backflow period, the estimated fluid information is calculated on the basis of the corrected average frequency signal obtained by correcting the average frequency signal.

As explained above, in the backflow period, the intensity of the scattered light changes, temporarily significantly. Thus, even if the average frequency signal obtained from the received light signal is used without a change to estimate the flow volume or the flow velocity, there is a possibility that an accurate value cannot be obtained. In contrast, if the corrected average frequency signal is used in the backflow period, it is possible to suppress an influence of the change in the received light intensity due to the backflow, and to accurately estimate the flow volume or the flow velocity.

<4>

In an aspect in which the corrected average frequency signal is used in the backflow period described above, the corrected average frequency signal may be a signal obtained by multiplying the average frequency signal by a predetermined coefficient.

According to the studies by the present inventors, it has been found that the average frequency signal when the backflow occurs has a waveform obtained by being folded on a centerline which is a defined level (e.g., zero). Thus, if the corrected average frequency signal is generated by multiplying the average frequency signal by the predetermined coefficient, it is possible to suppress the influence of the backflow and to accurately estimate the flow volume or the flow velocity.

The "predetermined coefficient" here may be a value set to bring the average frequency signal when the backflow occurs closer to a true value, and may be set, for example, as a value which is greater than or equal to −1 and is less than 1 including zero (−1≤Predetermined coefficient K<1). If the predetermined coefficient is "−1", the corrected average frequency signal is generated as a signal obtained by inverting the polarity of the average frequency signal.

Alternatively, the corrected average frequency signal may be an average value of the latest average frequency signal in a defined section.

<5>

In another aspect of the fluid measuring apparatus according to the embodiment,
the fluid measuring apparatus is further provided with an analyzing device configured to output an average frequency signal on the basis of the received light signal, wherein the calculating device is configured to calculate first fluid information on the basis of the average frequency signal and second fluid information by correcting the first fluid information, (i) to output the first fluid information as the estimated fluid information in a period other than a backflow period in which the backflow of the fluid is detected, and (ii) to output the second fluid information as the estimated fluid information in the backflow period.

According to this aspect, the first fluid information is firstly calculated on the basis of the average frequency signal obtained from the received light signal, and the second fluid information is further calculated by correcting the first fluid information. In other words, the two types of fluid information are separately calculated, regardless of whether or not the backflow occurs.

If the first fluid information and the second fluid information are calculated, the occurrence of the backflow is detected. Then, in the period other than the backflow period, the first fluid information (i.e., the fluid information calculated on the basis of the average frequency signal) is outputted as the estimated fluid information. On the other hand, in the backflow period, the second fluid information (i.e., the fluid information obtained by correcting the first fluid information) is outputted as the estimated fluid information.

As described above, it is possible to suppress the influence of the change in the received light intensity due to the backflow, and to output the estimated fluid information that is accurate, by outputting the second fluid information obtained by the correction in the backflow period.

<6>

In an aspect in which the first fluid information and the second fluid information are selectively outputted described above, the second fluid information may be information obtained by inverting a polarity of the first fluid information.

According to the studies by the present inventors, it has been found that the average frequency signal when the backflow occurs has a waveform obtained by being folded on a centerline which is a defined level (e.g., zero). Thus, the fluid information calculated from the average frequency signal when the backflow occurs may be calculated in a situation in which the polarity is determined.

On the other hand, if the polarity of the average frequency signal is inverted to generate the corrected average frequency signal, it is possible to suppress the influence of the backflow and to accurately estimate the flow volume or the flow velocity.

Moreover, in order to satisfy a relation of "the corrected average frequency signal<the average frequency signal before the correction", if the average frequency signal before the correction is multiplied by the predetermined coefficient K including zero (e.g., $-1 \leq K < 1$) to generate the corrected average frequency signal, it is then possible to more effectively suppress the influence of the backflow. If the polarity of the average frequency signal is inverted by using the predetermined coefficient K set as a negative value, it is not necessary to generate the second fluid information having an inverted polarity.

<7>

In another aspect of the fluid measuring apparatus according to the embodiment, the fluid measuring apparatus is further provided with: an average calculating device configured to average the estimated fluid information past and to calculate average fluid information; and a limiting device configured to limit a backflow period in which the backflow of the fluid is detected to be shorter as a flow volume or a flow velocity of the fluid indicated by the average fluid information increases.

According to the studies by the present inventors, it has been found that backflow detection accuracy more likely has an error as the flow volume or the flow velocity of the fluid indicated by the average fluid information increases, and that the backflow is more likely detected even when the backflow does not occur.

According to this aspect, the backflow period is limited to be shorter (in other words, the backflow is hardly detected) as the flow volume or the flow velocity of the fluid indicated by the average fluid information increases. It is thus possible to accurately detect the backflow even if the average fluid information indicates a high flow volume or a high flow velocity of the fluid.

<8>

In an aspect in which the backflow is detected by using the predetermined value described above, the fluid measuring apparatus may be further provided with: an average calculating device configured to average the estimated fluid information past and to calculate average fluid information; and a changing device configured to change the predetermined value to be higher as a flow volume or a flow velocity of the fluid indicated by the average fluid information increases.

In this case, the predetermined value is changed to be higher as the flow volume or the flow velocity of the fluid indicated by the average fluid information increases, and the backflow is hardly detected. It is therefore possible to accurately detect the backflow even if the average fluid information indicates a high flow volume or a high flow velocity of the fluid.

<9>

In another aspect of the fluid measuring apparatus according to the embodiment, the light receiving device includes: a first light receiving element and a second light receiving element, the detecting device is configured to detect the backflow of the fluid on the basis of a first received light signal outputted from the first light receiving element, and the calculating device is configured to calculate the estimated fluid information on the basis of the detection result of said detecting device and a second received light signal outputted from the second light receiving element.

According to this aspect, the first received light signal for detecting the backflow and the second received light signal for calculating the estimated fluid information are received by the light receiving elements that are different from each other (the first light receiving element and the second light receiving element). It is thus possible to respectively perform preferable processes on the signals, resulting in an improvement in a signal-noise (S/N) ratio.

<10>

A second fluid measuring apparatus according to the embodiment is provided with: an irradiating device configured to irradiate a fluid with light; a light receiving device configured to receive light scattered by the fluid; a detecting device configured to detect that a change amount of received light intensity indicated by a received light signal of the light receiving device is greater than or equal to a predetermined value; and a calculating device configured to calculate estimated fluid information indicating a flow volume or a flow velocity of the fluid, on the basis of a detection result of the detecting device and the received light signal of the light receiving device.

According to the second fluid measuring apparatus in the embodiment, it is detected that the change amount of the received light intensity indicated by the received light signal of the light receiving device is greater than or equal to the predetermined value, and the estimated fluid information is calculated on the basis of the detection result. If the change amount of the received light intensity is greater than or equal to the predetermined value, it is hard to accurately estimate the flow volume or the flow velocity on the basis of the received light signal. Thus, if it can be detected that change amount of the received light intensity is greater than or equal to the predetermined value, it is possible to suppress deterioration in estimation accuracy of the flow volume or the flow velocity of the fluid.

Therefore, according to the second fluid measuring apparatus in the embodiment, as in the first fluid measuring apparatus in the embodiment described above, it is possible to accurately estimate the flow volume or the flow velocity of the fluid. The second fluid measuring apparatus in the embodiment can also adopt the same various aspects as those of the first fluid measuring apparatus in the embodiment described above.

The operation and other advantages of the fluid measuring apparatus according to the embodiments will be explained in more detail in the following practical example.

PRACTICAL EXAMPLES

Hereinafter, a fluid measuring apparatus according to practical examples will be explained in detail with reference to the drawings.

First Practical Example

A fluid measuring apparatus according to a first practical example will be explained with reference to FIG. 1 to FIG. 10. Hereinafter, an explanation will be given to an example in which the fluid measuring apparatus is configured to be an apparatus for measuring a blood flow volume.

<Entire Configuration>

Firstly, with reference to FIG. 1, an entire configuration of the fluid measuring apparatus according to the first practical example will be explained. Here, FIG. 1 is a schematic diagram illustrating the entire configuration of the fluid measuring apparatus according to the first practical example.

In FIG. 1, the fluid measuring apparatus according to the first practical example is provided with a laser drive unit 110, a semiconductor laser 120, a first light receiving element 131, a first I-V converter 141, a LPF amplifier 151, a BPF amplifier 152, a first A/D converter 161, a second A/D converter 162, and a backflow correction flow volume estimator 300.

The laser drive unit 110 is configured to generate an electric current for driving the semiconductor laser 120.

The semiconductor laser 120 is a specific example of the "irradiating device", and is configured to irradiate a target 200 to be measured (e.g., a blood flow, etc.) with laser light corresponding to a drive current generated on the laser drive unit 110.

The first light receiving element 131 is a specific example of the "light receiving device", and is configured to receive scattered light scattered by a blood 200 (mainly, reflected light including back-scattered light), out of the laser light emitted from the semiconductor laser 120. The first light receiving element 131 is configured to output a detected current in accordance with the intensity of reflected light received.

The first I-V converter 141 is configured to convert the detected current, which is outputted from the first light receiving element 131, to a voltage, and to output a detected voltage.

The first LPF amplifier 151 is configured to remove a high frequency component, which is an unnecessary component including noise, from the detected voltage inputted, and to amplify and output it as a scattered DC signal. On the other hand, the BPF amplifier 152 is configured to remove a high frequency component and a low frequency component, which are unnecessary components including noise, from the detected voltage inputted, and to amplify and output it as a scattered AC signal.

The first A/D converter 161 is configured to quantize the scattered DC signal and to output it as a scattered DC light amount RDC to the backflow correction flow volume estimator 300. The second A/D converter 162 is configured to quantize the scattered AC signal and to output it as a scattered AC light amount RAC to the backflow correction flow volume estimator 300.

The backflow correction flow volume estimator 300 is provided with a backflow detector 310 and a correction processor 320. The backflow correction flow volume estimator 300 is configured to detect a backflow of the target 200 to be measured, by using a temporal change in the scattered DC light amount RDC inputted. The backflow correction flow volume estimator 300 is also configured to obtain an average frequency by frequency-analyzing the scattered AC light amount RAC inputted, and to estimate a flow volume of the target 200 to be measured from the average frequency. An estimated flow volume Q calculated on the backflow correction flow volume estimator 300 is outputted to an external apparatus (e.g., a display, etc.).

<Configuration and Operation of Each Unit>

Next, with reference to FIG. 2 to FIG. 8, the configuration and operation of each unit of the fluid measuring apparatus will be explained in detail.

<Light Receiving Element and I-V Converter>

Figure 2:
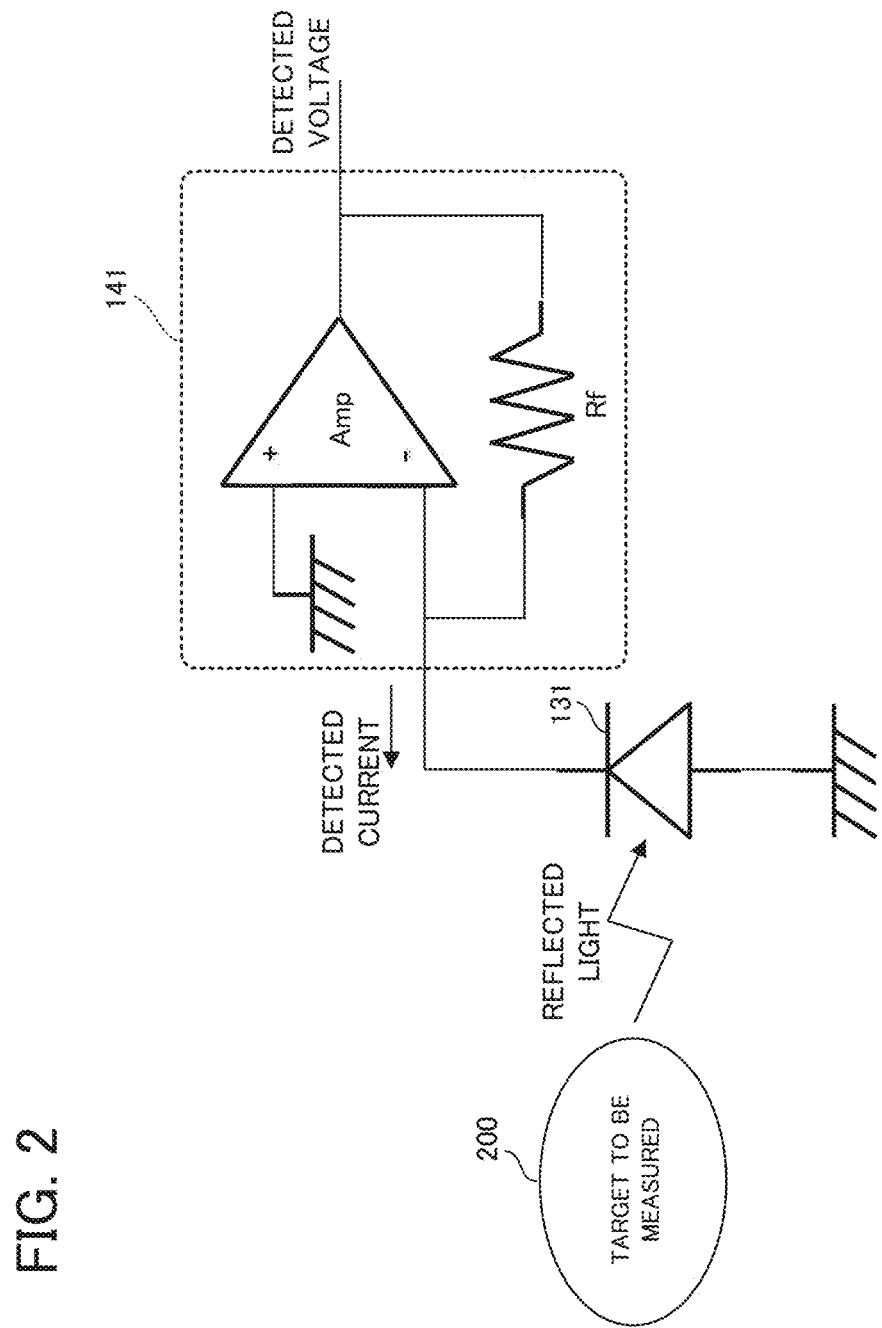
FIG. 2 is a circuit diagram illustrating a configuration of a first light receiving element and a first I-V converter.

With reference to FIG. 2, the configuration and operation of the light receiving element and the I-V converter will be explained. FIG. 2 is a circuit diagram illustrating the configuration of the first light receiving element and the first I-V converter.

As illustrated in FIG. 2, the reflected light mainly including the back-scattered light out of the scattered light from the target 200 to be measured may be detected on the first light receiving element 131.

The first light receiving element 131 includes a photodetector by a semiconductor. An anode of the photodetector is connected to a ground potential, which is a reference potential, whereas a cathode of the photodetector is connected to an inverted terminal of an operational amplifier Amp. A non-inverted terminal of the operational amplifier Amp is connected to the ground potential, which is the reference potential.

A feedback resistor Rf is connected between the inverted terminal and an output terminal of the operational amplifier Amp. The operational amplifier Amp and the feedback resistor Rf constitute a so-called transimpedance amplifier. By a current-voltage converting action of the transimpedance amplifier, the detected current is converted to the detected voltage.

<Backflow Detector>

Figure 3:
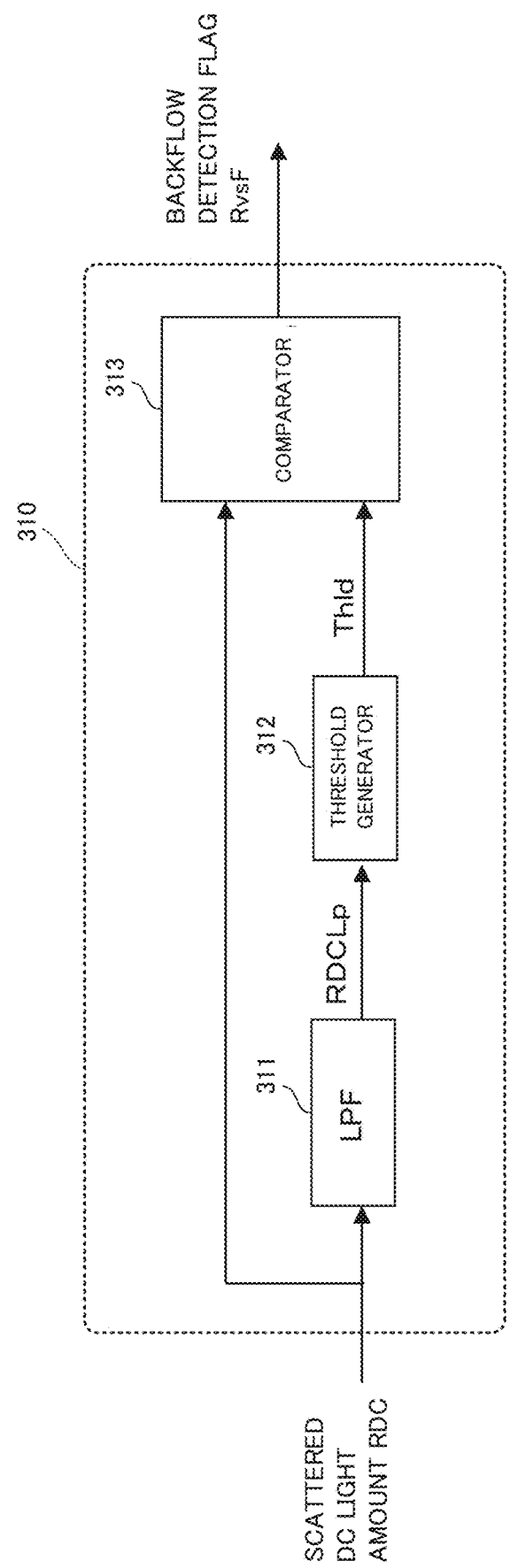
FIG. 3 is a block diagram illustrating a configuration of a backflow detector according to the first practical example.

With reference to FIG. 3, the configuration and operation of the backflow detector will be explained. FIG. 3 is a block diagram illustrating the configuration of the backflow detector according to the first practical example.

As illustrated in FIG. 3, the backflow detector 310 is provided with a low pass filter (LPF) 311, a threshold generator 312, and a comparator 313. The backflow detector 310 is a specific example of the "detecting device".

The scattered DC light amount RDC inputted to the backflow detector 310 is averaged by the LPF 311 to obtain a scattered DC light amount average value RDCLp. The RDCLp is outputted to the threshold generator 312.

The threshold generator 312 is configured to multiply the inputted past scattered DC light amount average value RDCLp by a predetermined coefficient (e.g., 0.9) to generate a threshold value Thld. The threshold value Thld is a specific example of the "predetermined value", and is generated as a value for detecting a rapid change in the scattered DC light amount RDC.

The comparator 313 is configured to receive an entry of the scattered DC light amount RDC that does not pass through the LPF 311, and an entry of the threshold value Thld. The comparator 313 is configured to detect a rapid reduction in the scattered DC light amount RDC by comparing magnitude between the scattered DC light amount RDC and the threshold value Thld. If the rapid reduction in the scattered DC light amount RDC is detected, it is determined that the backflow occurs, and a backflow detection flag RvsF=1 is outputted from the comparator 313. On the other hand, if the rapid reduction in the scattered DC light amount RDC is not detected (i.e., the temporal change in the scattered DC light amount RDC is mild and the change is small), it is determined that the backflow does not occur, and a backflow detection flag RvsF=0 is outputted from the comparator 313.

The backflow detection flag RvsF, which is a detection result of the backflow detector 310, is inputted to a control input of the correction processor 320.

<Correction Processor>

Figure 4:
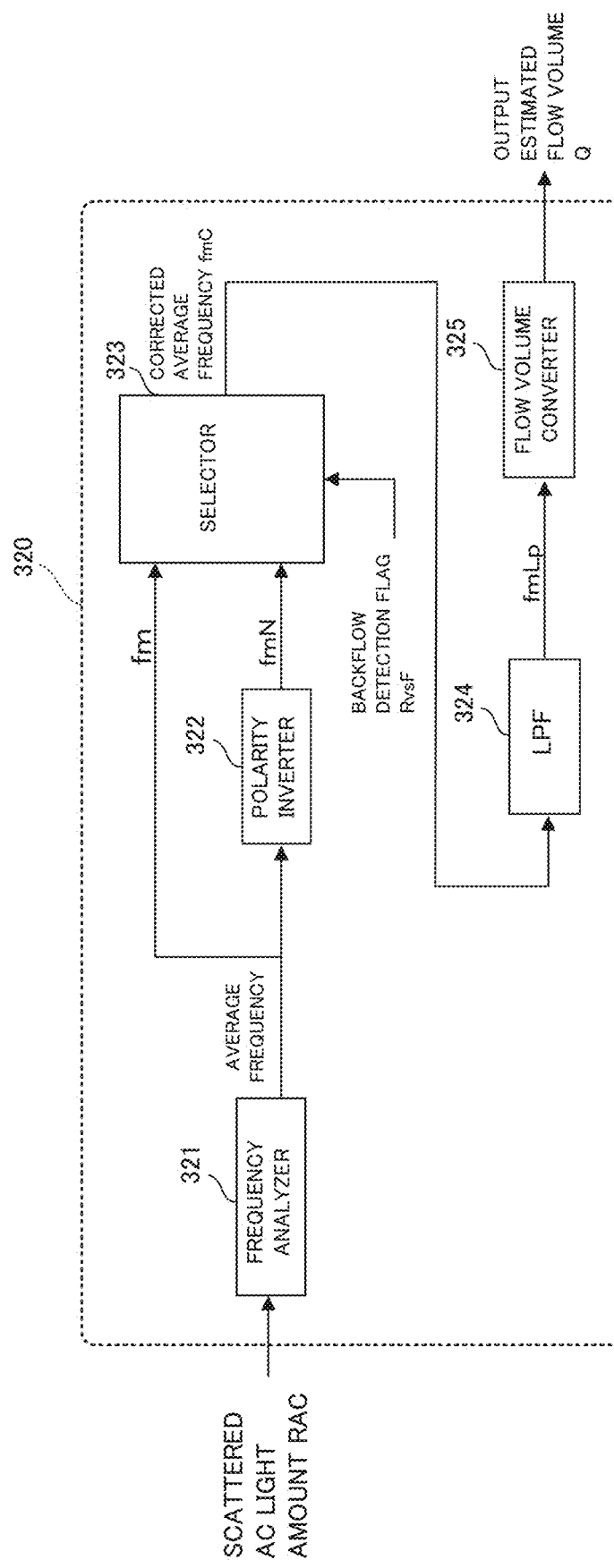
FIG. 4 is a block diagram illustrating a configuration of a correction processor according to the first practical example.

With reference to FIG. 4, the configuration and operation of the correction processor will be explained. FIG. 4 is a block diagram illustrating the configuration of the correction processor according to the first practical example.

As illustrated in FIG. 4, the correction processor 320 is provided with a frequency analyzer 321, a polarity inverter 322, a selector 323, a LPF 324, and a flow volume converter 325. The correction processor 320 is a specific example of the "calculating device".

The scattered AC light amount RAC inputted to the correction processor 320 is frequency-analyzed by the frequency analyzer 321. The frequency analyzer 321 is configured to output an analysis result as an average frequency fm. The average frequency fm is inputted to the polarity inverter 322 and the selector 333.

The polarity inverter 322 is configured to invert a polarity of the average frequency. Specifically, the polarity inverter 322 may invert the average frequency with a positive polarity to an inverted average frequency fmN with a negative polarity, and to output it. The inverted average frequency fmN is outputted to the selector 323.

The selector 323 is configured to selectively output any of the average frequency fm and the polarity-inverted fmN as a corrected average frequency fmC, in accordance with the backflow detection flag RvsF detected on the backflow detector 310.

Specifically, if the backflow detection flag RvsF=1, it is determined that the backflow occurs, and the polarity-inverted fmN is selectively outputted. On the other hand, if the backflow detection flag RvsF=0, it is determined that the backflow does not occur, and the fm with the polarity being not inverted is selectively outputted.

The corrected average frequency fmC is inputted and averaged by the LPF 324. An output of the LPF, fmLp, is converted to a flow volume by the flow volume converter 325 and is outputted as the estimated flow volume Q.

The polarity inverter 322 performs a process of simply multiplying the average frequency fm by "−1" only to invert the polarity; however, instead of this process, the polarity inverter 322 may perform a process of multiplying the average frequency fm by a predetermined coefficient K. In other words, fmN=K×fm may be satisfied. The predetermined coefficient K here can be selected in a range of −1≤K<1.

<Frequency Analyzer>

Figure 5:
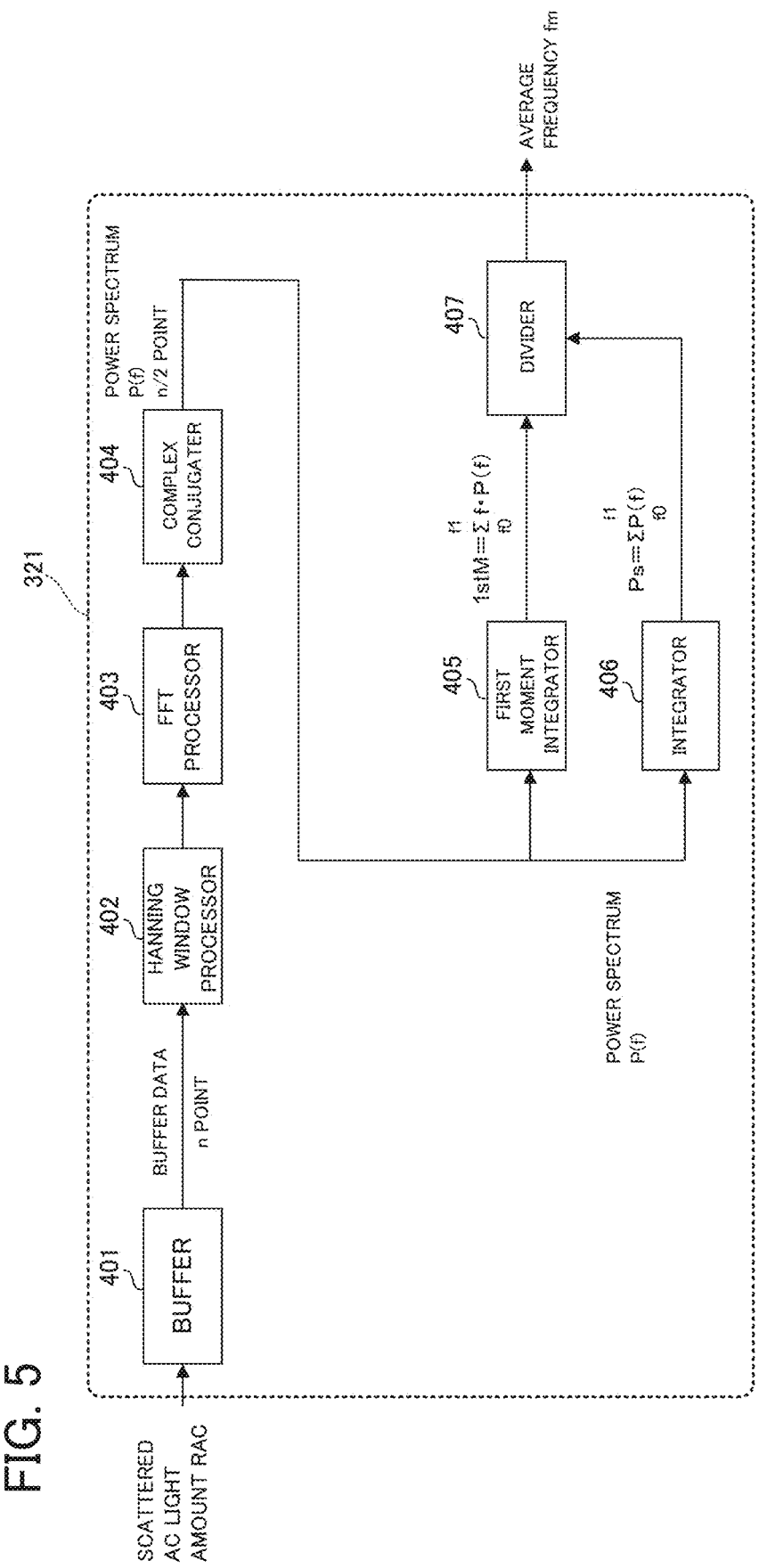
FIG. 5 is a block diagram illustrating a configuration of a frequency analyzer.

With reference to FIG. 5, the configuration and operation of the frequency analyzer will be explained. FIG. 5 is a block diagram illustrating the configuration of the frequency analyzer.

As illustrated in FIG. 5, the frequency analyzer 321 is provided with a buffer 401, a hanning window processor 402, a Fast Fourier Transform (FFT) processor 403, a complex conjugate 404, a first moment integrator 405, an integrator 406, and a divider 407. The frequency analyzer 321 is a specific example of the "average calculating device".

The scattered AC light amount RAC data is stored by the buffer 401. A data array of n points stored in the buffer 401 is multiplied by a window function by the Hanning window processor 402, and FFT of n points is performed by the FFT processor 403.

An analysis result outputted by the FFT processor 403 is changed by the complex conjugate 404 into a power spectrum P(f), which is then outputted. The power spectrum P(f) is multiplied by a frequency vector and is integrated on the first moment integrator 405, and a first moment 1stM is outputted. Moreover, the power spectrum P(f) is integrated on the integrator 406, and an integrated value Ps is outputted. The first moment 1stM is divided by the integrated value Ps on the divider 407, and the average frequency fm is outputted.

<Method of Calculating Flow Volume>

Figure 6:
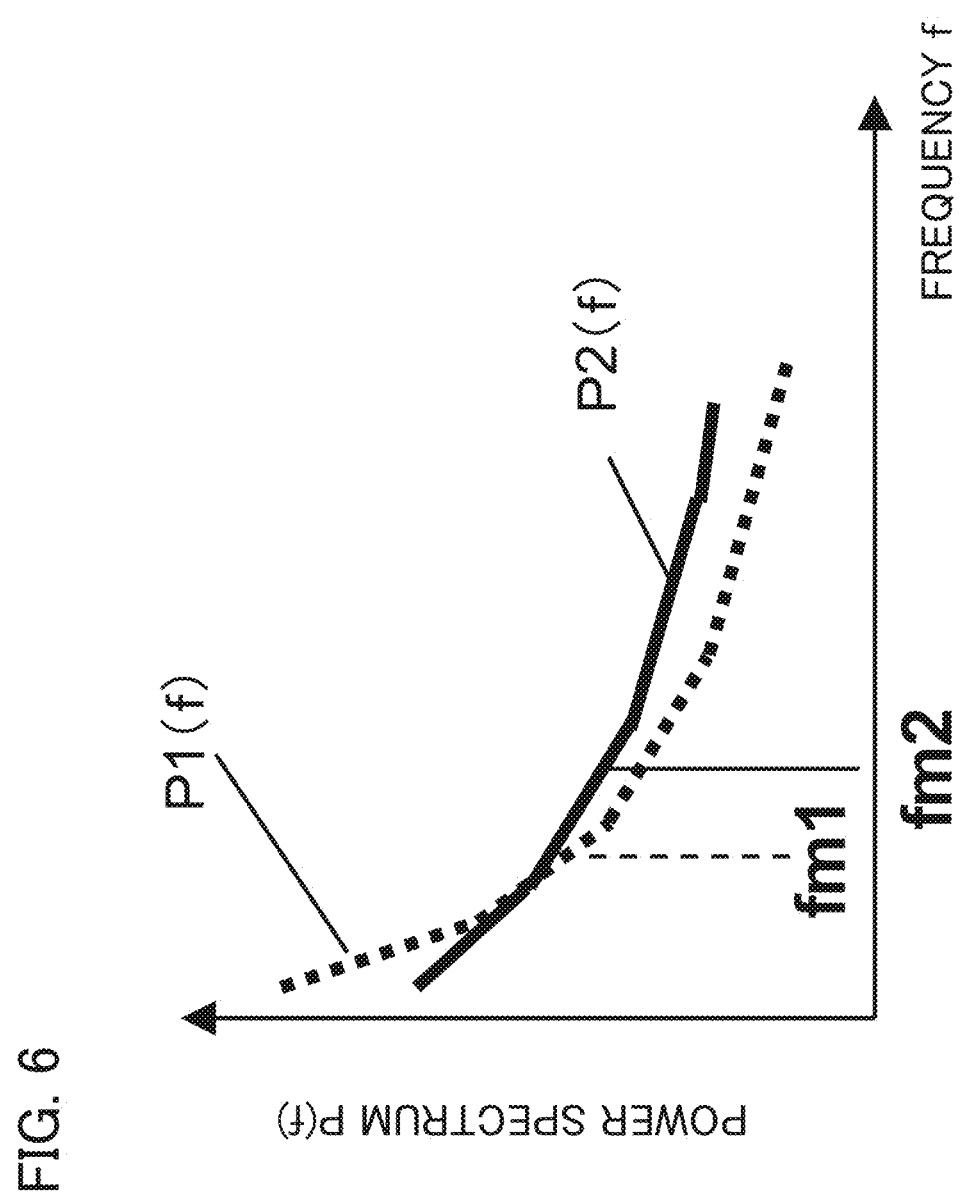
FIG. 6 is a graph illustrating a relation between a frequency f and a power spectrum P(f).
Figure 7:
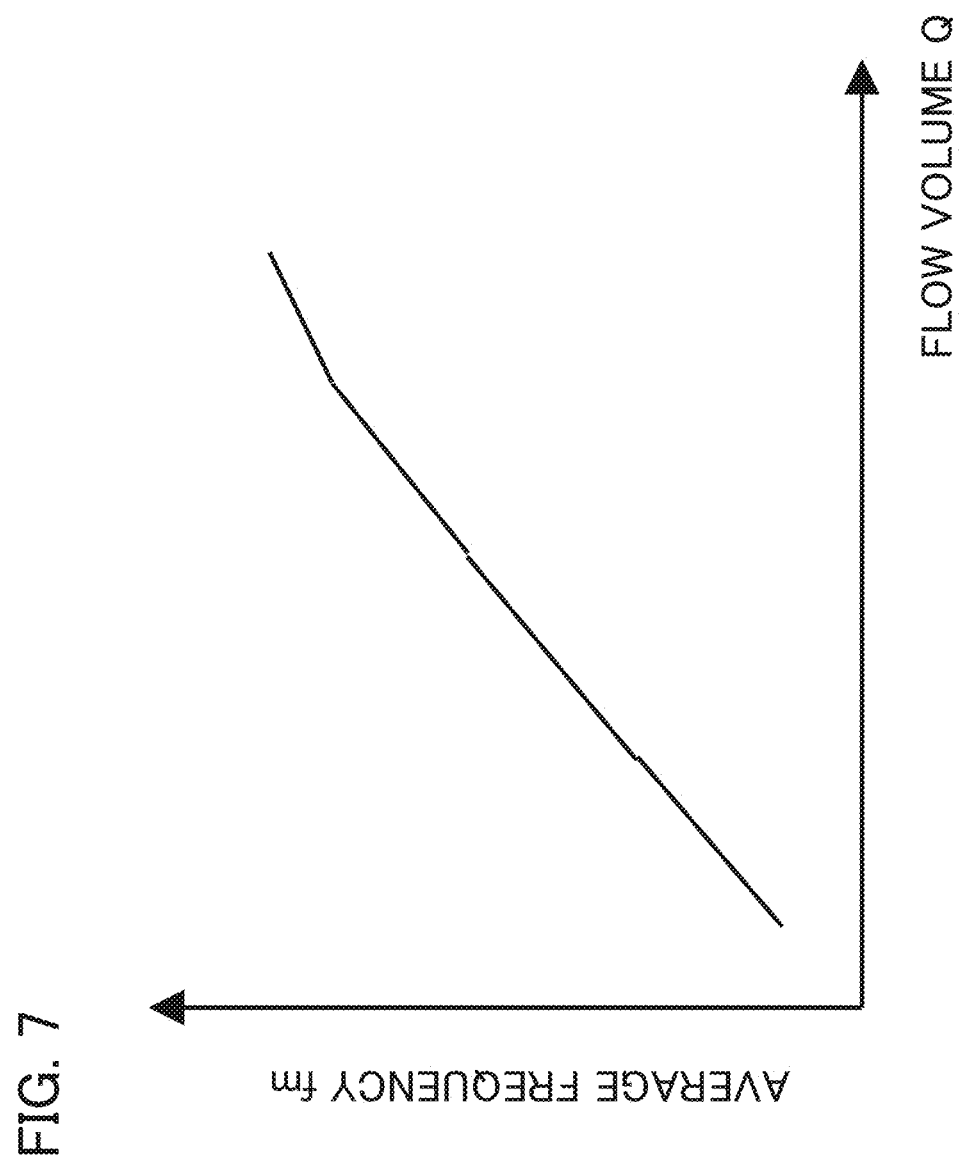
FIG. 7 is a graph illustrating a relation between a flow volume Q and an average frequency fm.

Here, with reference to FIG. 6 and FIG. 7, a method of calculating the estimated flow volume Q will be more specifically explained. FIG. 6 is a graph illustrating a relation between a frequency f and the power spectrum P(f). FIG. 7 is a graph illustrating a relation between a flow volume Q and the average frequency fm.

If the target 200 to be measured has a high flow velocity, which is a high moving speed, then, the scattered laser light has a high frequency by the action of Optical Doppler shift. On the other hand, a flow passage of the target 200 to be measured (e.g., a transparent tube) is fixed and is not moved. Thus, the laser light scattered by the transparent tube is not Doppler-shifted, and the frequency is not shifted.

Both of the scattered lights interfere on the first light receiving element 131 due to coherence of the laser light. As a result, the first light receiving element 131 may receive an optical beat signal corresponding to the flow velocity, which is the moving speed, of the target 200 to be measured. The scattered AC light amount RAC is a signal obtained by amplifying and quantifying the optical beat signal. Therefore, the frequency analysis of the scattered AC light amount RAC provides the power spectrum P(f), from which it is possible to estimate the flow volume corresponding to the moving speed of the target 200 to be measured. In the first practical example, a flow volume estimating apparatus is configured by laser flowmetry.

As illustrated in FIG. 6, the power spectrum P(f) of the optical beat signal varies depending on the moving speed of the target 200 to be measured. Specifically, the power spectrum P(f) in a lower flow velocity with a slow moving speed concentrates on a lower frequency. The power spectrum P(f) in the lower flow velocity is expressed as P1($f$) in a dotted line. On the other hand, the power spectrum in a higher flow velocity with a high moving speed concentrates on a higher frequency. The power spectrum P(f) in the higher flow velocity is expressed as P2($f$) in a solid line.

As is clear from the drawing, P1($f$)>P2($f$) is satisfied in a low frequency area, and P2($f$)>P1($f$) is satisfied in a high frequency area. If an average frequency fm1 of the power spectrum P1($f$) in the lower velocity and an average frequency fm2 of the power spectrum P2($f$) in the higher velocity are calculated and compared by the frequency analysis, fm1<fm2 is satisfied.

As illustrated in FIG. 7, as the flow volume Q increases, the average frequency fm increases. By using this relation, it is possible to calculate the estimated flow volume Q from the average frequency fm obtained by the frequency analysis.

<Specific Example of Backflow Detection and Correction Process>

Figure 8:
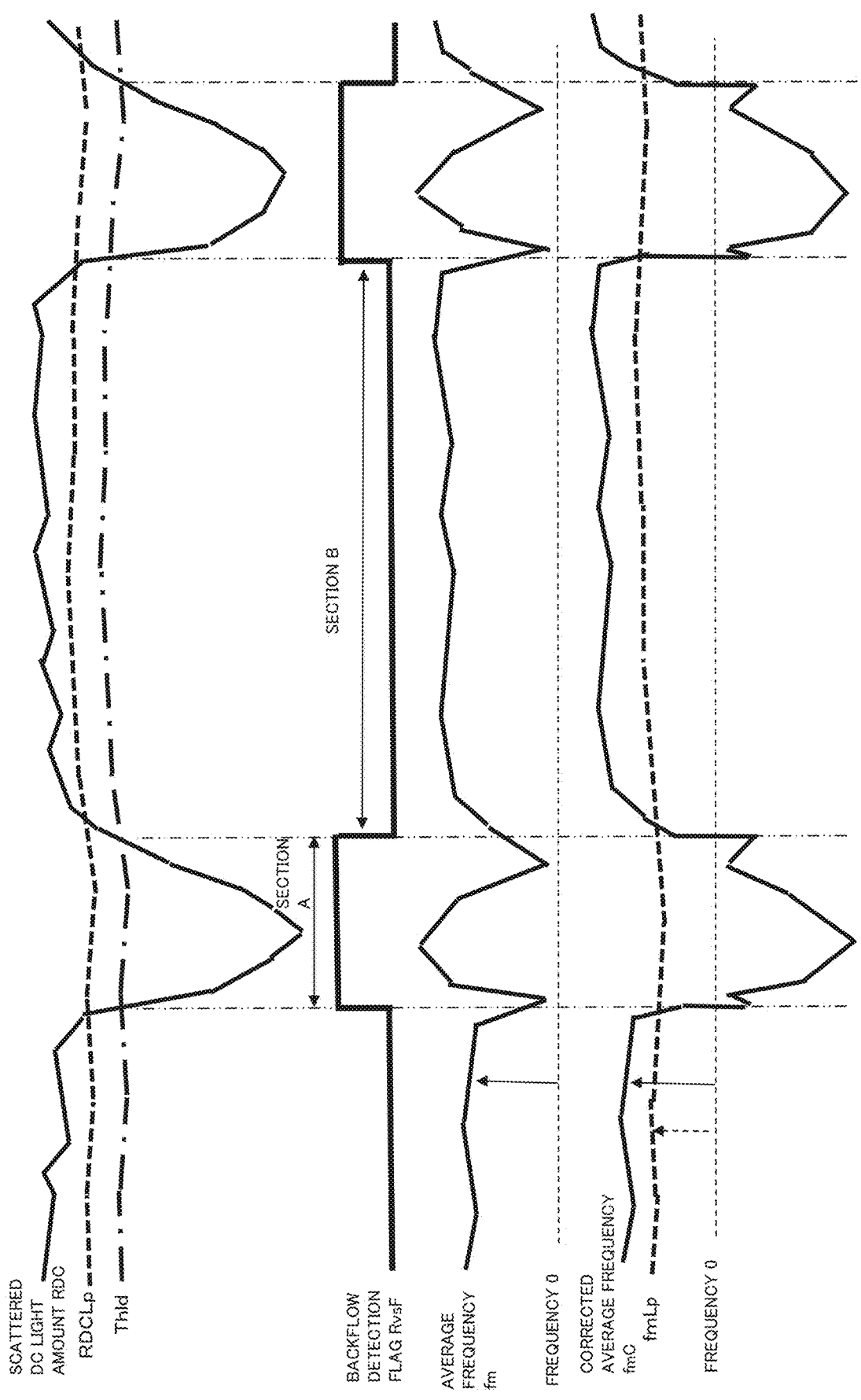
FIG. 8 is a graph illustrating an example of a temporal variation in each signal regarding a light amount.

Next, with reference to FIG. 8, the backflow detection performed by the backflow detector 310 and the correction process performed by the correction processor 320 will be more specifically explained. FIG. 8 is a graph illustrating an example of a temporal variation in each signal regarding the light amount.

The blood, which is the target 200 to be measured according to the first practical example, flows in a tube by a power of a tube pump (not illustrated). The tube pump transfers the fluid in the tube, by a plurality of rollers squeezing the tube by rotation. From the structural viewpoint of the pump, pulsation occurs in synchronization with the rotation. The pulsation may cause the backflow of the blood. Specifically, the fluid repeatedly flows backward and forward, and is generally transferred in a forward direction; however, there is a section in which the fluid moves in an opposite direction due to the backflow for a short time in synchronization with the rotation. If the backflow occurs, it is considered that a compressional wave in a fluid concentration caused by the pulsation of the pump changes from being dense to being sparse, which causes a rapid reduction in the reflected light amount, which is the light amount of the scattered light, for example, the back-scattered light.

In FIG. 8, in a section A, the scattered DC light amount RDC rapidly decreases beyond the threshold value Thld, so that the backflow supposedly occurs. Thus, in the section A, the fmN obtained by inverting the polarity of the average frequency fm is outputted as the corrected average frequency fmC.

In contrast, in a section B, the scattered DC light amount RDC has a mild temporal change, so that the flow is supposedly in a stable dense state and the backflow supposedly does not occur. Thus, in the section B, the average frequency fm is outputted without a change as the corrected average frequency fmC.

As is clear from the drawing, it is possible to eliminate an influence of the backflow by outputting the inverted average frequency fmN in the section A.

<Effect of First Practical Example>

Figure 9:
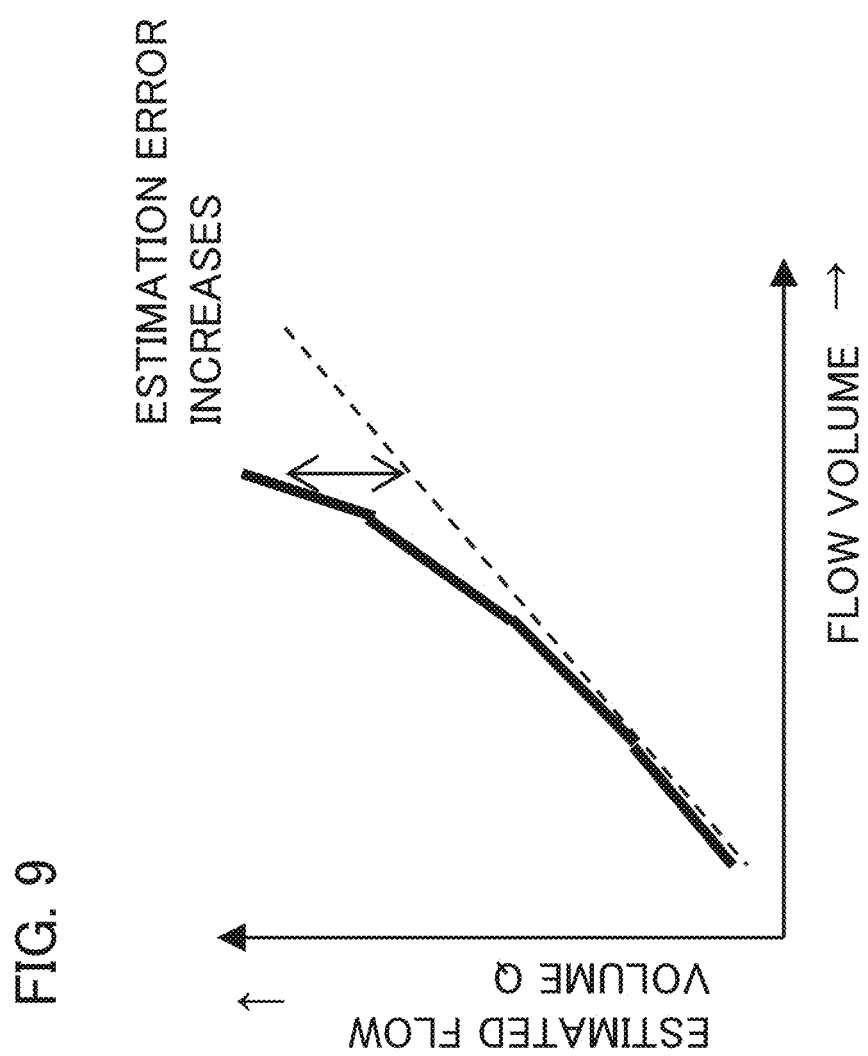
FIG. 9 is a graph illustrating an estimation error of the flow volume according to a comparative example.
Figure 10:
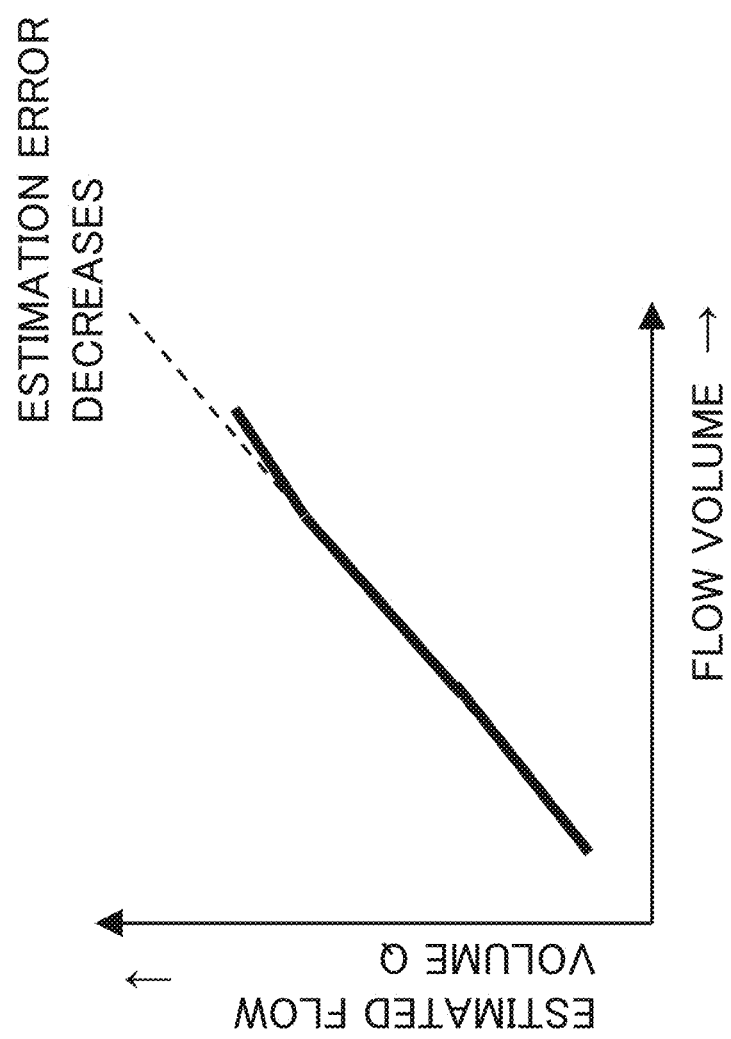
FIG. 10 is a graph illustrating an estimation error of the flow volume according to the first practical example.

Next, with reference to FIG. 9 and FIG. 10, a technical effect obtained by the fluid measuring apparatus according to the first practical example will be explained. FIG. 9 is a graph illustrating an estimation error of the flow volume according to a comparative example. FIG. 10 is a graph illustrating an estimation error of the flow volume according to the first practical example.

As explained above, if the backflow occurs in the target 200 to be measured, there may be an error in the estimated flow volume Q. Particularly in the artificial dialysis apparatus, if a blood removing needle is thin in diameter, if the pump has a high number of revolutions, and if a set flow volume is high, then, a backflow amount increases and the estimation error further increases, which has been experimentally confirmed.

As illustrated in FIG. 9, unlike the first practical example, if the average frequency fm is not corrected by detecting the backflow, the occurrence of the backflow increases the estimation error of the estimated flow volume Q.

In contrast, in the first practical example, if the backflow is detected, the process of replacing the average frequency fm by the inversed average frequency fmN is performed. As a result, a waveform of the corrected average frequency fmC is normal even in a backflow occurrence section (e.g. refer to FIG. 8, etc.).

As illustrated in FIG. 10, if the average frequency fm is corrected by detecting the backflow, the estimation error of the estimated flow volume is reduced, and satisfactory characteristics are shown.

As explained above, according to the fluid measuring apparatus in the first practical example, even if the backflow temporarily occurs in the fluid, the flow volume Q can be accurately estimated.

Second Practical Example

Figure 11:
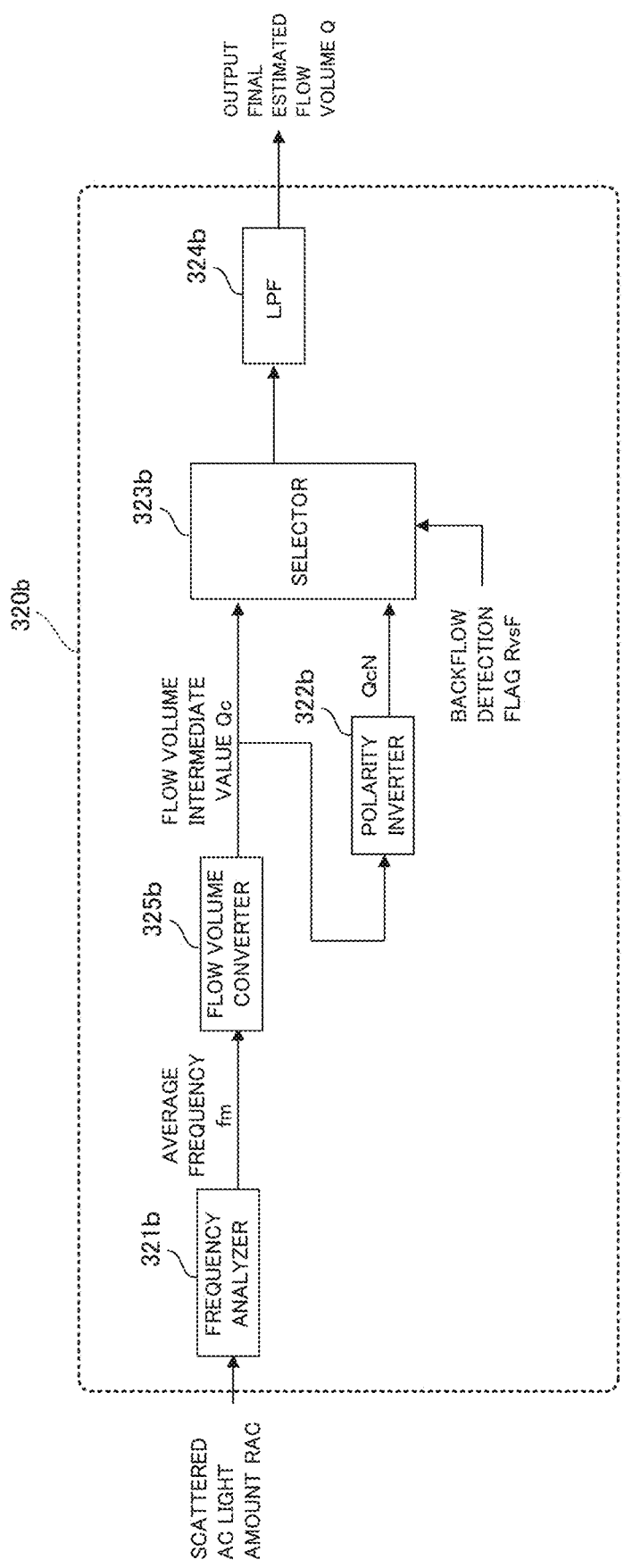
FIG. 11 is a block diagram illustrating a configuration of a correction processor according to a second practical example.

A fluid measuring apparatus according to a second practical example will be explained with reference to FIG. 11. FIG. 11 is a block diagram illustrating a configuration of a correction processor according to the second practical example.

The second practical example is different only in the configuration and operation of the correction processor from the first practical example, and is substantially the same as the first practical example in the other part. Thus, hereinafter, the different part from that of the first practical example will be explained in detail, and an explanation of the same part will be omitted as occasion demands.

As illustrated in FIG. 11, a correction processor 320b is provided with a frequency analyzer 321b, a polarity inverter 322b, a selector 323b, an LPF 324b, and a flow volume converter 325b. Particularly in the second practical example, the flow volume converter 325b is provided before the polarity inverter 322b and the selector 323b, and the average frequency fm outputted from the frequency analyzer 321b is inputted to the flow volume converter 325b.

The flow volume converter 325b is configured to calculate a flow volume intermediate value Qc and to output it to both the polarity inverter 322b and the selector 323b. The flow volume converter 325b may calculate the flow volume intermediate value Qc in the same method as the method of calculating the estimated flow volume Q used by the flow volume converter 325 in the first practical example.

The selector 323b is configured to receive an entry of the flow volume intermediate value Qc and an entry of an inverted flow volume intermediate value QcN obtained by inverting the polarity on the polarity inverter 322b. The selector 323b is also configured to receive an entry of the backflow detection flag RvsF, which is outputted from the backflow detector 310, and to selectively output the flow volume intermediate value Qc or the flow volume intermediate value QcN in accordance with the backflow detection flag RvsF.

Specifically, the selector 323b is configured to output the flow volume intermediate value QcN in a backflow period in which RvsF=1 is inputted. On the other hand, the selector 323b is configured to output the flow volume intermediate value Qc in a period in which RvsF=0 is inputted when the backflow does not occur.

The flow volume intermediate value Qc or the flow volume intermediate value QcN outputted from the selector 323b is averaged on the LPF 324b, so that discontinuity in selective control is removed. It is then outputted as a final estimated flow volume Q.

As explained above, on the fluid measuring apparatus according to the second practical example, unlike the first practical example, not the average frequency fm but the estimated flow volume calculated from the average frequency fm is corrected. Even in this case, as in the first practical example, it is possible to reduce an influence by the occurrence of the backflow, and it is possible to accurately estimate the flow velocity of the target 200 to be measured.

Third Practical Example

Figure 12:
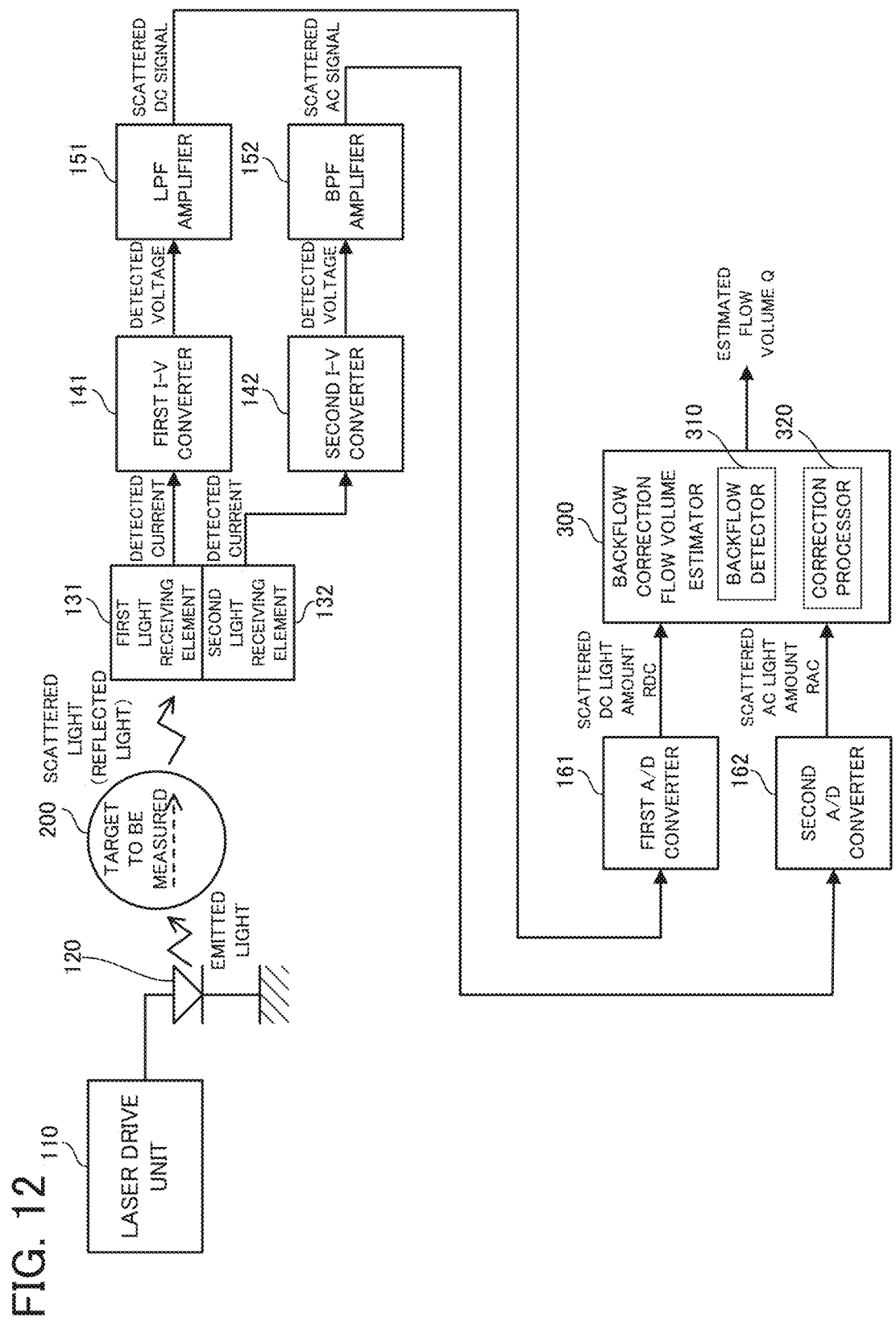
FIG. 12 is a schematic diagram illustrating an entire configuration of a fluid measuring apparatus according to a third practical example.

A fluid measuring apparatus according to a third practical example will be explained with reference to FIG. 12. FIG. 12 is a schematic diagram illustrating an entire configuration of a fluid measuring apparatus according to a third practical example.

The third practical example is partially different only in the configuration and operation near the light receiving element from the first and second practical examples, and is substantially the same as the first and second practical examples in the other part. Thus, hereinafter, the different part from those of the first and second practical examples will be explained in detail, and an explanation of the same part will be omitted as occasion demands.

As illustrated in FIG. 12, the fluid measuring apparatus according to the third practical example is provided with not only the first light receiving element 131 but also a second light receiving element 132, as the element configured to receive the reflected light from the target to be measured. In other words, in the third practical example, two light receiving elements are provided.

A detected current outputted from the first light receiving element 131 is converted to a detected voltage on the first I-V converter 141 and is inputted to the LPF amplifier 151. On the other hand, a detected current outputted from the second light receiving element 132 is converted to a detected voltage on the second I-V converter 142 and is inputted to the BPF amplifier 152. As described above, in the third practical example, the first light receiving element 131 for obtaining the scattered DC signal and the second light receiving element 132 for obtaining the scattered AC signal are separately provided.

In the third practical example, a circuit for obtaining the scattered AC signal is formed separately from a circuit for obtaining the scattered DC signal. It is thus possible to preferably remove a DC component (e.g., a power supply noise, a hum signal, etc.) that could be included in the scattered AC signal. In order to remove the DC component, for example, it is possible to use a circuit configured to cancel the DC component by connecting two photodiodes opposite to each other.

As explained above, on the fluid measuring apparatus according to the third practical example, it is possible to improve the S/N ratio in comparison with the first practical example because the DC component can be preferably removed from the scattered AC signal.

Fourth Practical Example

Figure 13:
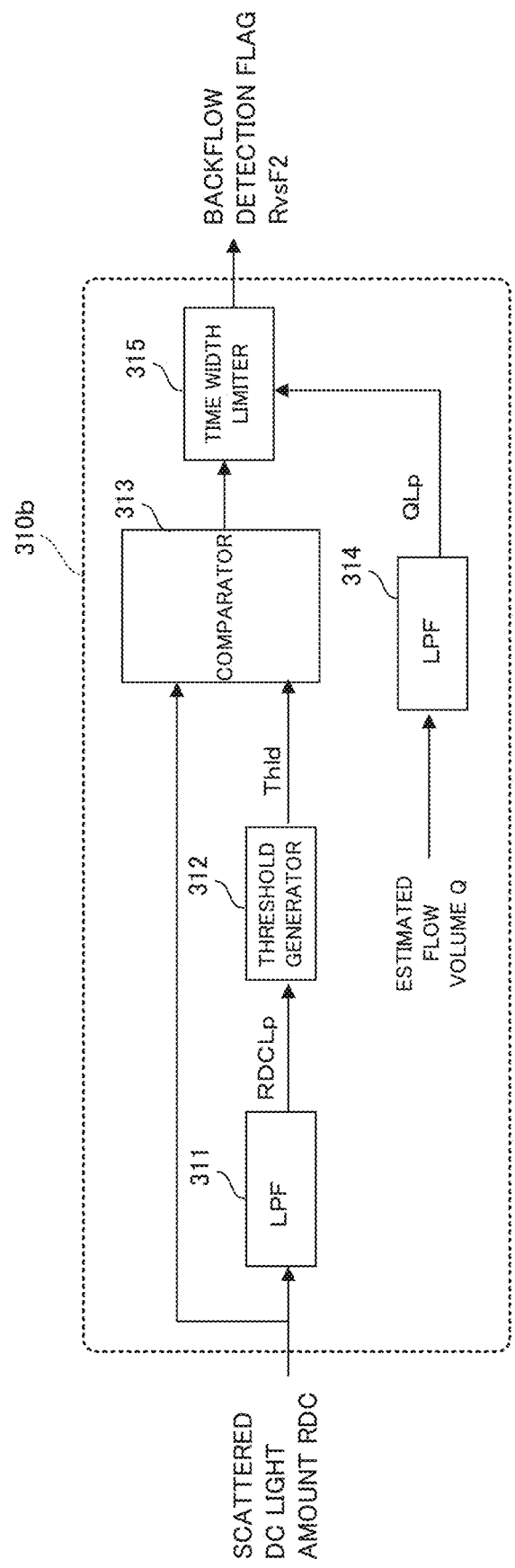
FIG. 13 is a block diagram illustrating a configuration of a backflow detector according to a fourth practical example.

Next, a fluid measuring apparatus according to a fourth practical example will be explained with reference to FIG. 13 and FIG. 14. FIG. 13 is a block diagram illustrating a configuration of a backflow detector according to a fourth practical example. FIG. 14 is a graph illustrating a method of limiting a time width regarding the detection of the backflow.

The fourth practical example is different only in the configuration and operation near the backflow detector from the first to third practical examples, and is substantially the same as the first to third practical examples in the other part. Thus, hereinafter, the different part from those of the first to third practical examples will be explained in detail, and an explanation of the same part will be omitted as occasion demands.

As illustrated in FIG. 13, a backflow detector 310b according to the fourth practical example is provided with a LPF 314 and a time width limiter 315, in addition to the configuration of the backflow detector 310 according to the first practical example (refer to FIG. 3). The LPF 314 is a specific example of the "average calculating device", and the time width limiter 315 is a specific example of the "limiting device".

On the backflow detector 310b according to the fourth practical example, an output of the comparator 313 itself is inputted to the time width limiter 315 without being outputted as the backflow detection flag RvsF. Moreover, the time width limiter 315 is configured to receive an entry of an average estimated flow volume QLp obtained by averaging the past estimated flow volume Q on the LPF 314.

The time width limiter 315 is configured to limit a pulse width outputted from the comparator 313, in accordance with the average estimated flow volume QLp, and to output it as the backflow detection flag RvsF. Specifically, if the average estimated flow volume QLp is high, the pump supposedly has a high rotation frequency and a relatively short backflow period. Thus, the width of the backflow period may be set to be relatively short (in other words, a limit amount may be set to be large). On the other hand, if the average estimated flow volume QLp is low, the pump supposedly has a low rotation frequency and a relatively long backflow period. Thus, the width of the backflow period may be set to be relatively long (in other words, a limit amount may be set to be small).

The same effect can be obtained by changing the threshold value Thld, instead of directly limiting the width of the backflow period. Specifically, if the average estimated flow volume QLp is high, it is hardly detected that the backflow occurs, by setting the threshold value Thld to be low. As a result, the backflow period is limited to have a relatively short width. On the other hand, if the average estimated flow volume QLp is low, it is easily detected that the backflow occurs, by setting the threshold value Thld to be high. As a result, the backflow period is limited to have a relatively long width.

As illustrated in FIG. 14, limiting the width of the backflow period may provide the corrected average frequency fmC with a smooth waveform. Specifically, a boundary is smoother between the backflow period and the period in which the backflow does not occur, in comparison with a case in which the width of the backflow period is not limited as illustrated in FIG. 8. This is considered to be a result of elimination of excessive correction of the flow volume correction.

In the example illustrated in the drawing, only a latter side of the backflow period is limited to be short; however, a former side of the backflow period may be limited to be short. According to studies by the present inventors, however, it has been found that limiting the latter side of the backflow period exhibits a higher effect than that of limiting the former side.

As explained above, on the fluid measuring apparatus according to the fourth practical example, it is possible to estimate the flow volume, more accurately, by limiting the width of the backflow period in accordance with the past estimated flow volume Q.

The present invention is not limited to the aforementioned embodiments and examples, but various changes may be made, if desired, without departing from the essence or spirit of the invention which can be read from the claims and the entire specification. A fluid measuring apparatus that involve such changes is also intended to be within the technical scope of the present invention.

DESCRIPTION OF REFERENCE NUMERALS AND LETTERS 110 laser drive unit
120 semiconductor laser
131 first light receiving element
132 second light receiving element
141 first I-V converter
142 second I-V converter
151 LPF amplifier
152 BPF amplifier
161 first A/D converter
162 second A/D converter
200 target to be measured
300 backflow correction flow volume estimator
310 backflow detector
320 correction processor

The invention claimed is:

1. A fluid measuring apparatus comprising:
an irradiating device configured to irradiate a fluid with light;
a light receiving device configured to receive light scattered by the fluid;
a detecting device configured to detect a backflow of the fluid based on a received light signal of said light receiving device when a change amount of received light intensity indicated by the received light signal is greater than or equal to a predetermined value;
a calculating device configured to calculate estimated fluid information indicating a flow volume or a flow velocity of the fluid, based on a detection result of said detecting device and the received light signal of said light receiving device;
an average calculating device configured to average previously-estimated fluid information and to calculate average fluid information; and
a changing device configured to change the predetermined value to be higher as a flow volume or a flow velocity of the fluid indicated by the average fluid information increases.

2. The fluid measuring apparatus according to claim 1, further comprising an analyzing device configured to output an average frequency signal based on the received light signal,
wherein said calculating device is configured (i) to calculate the estimated fluid information based on the average frequency signal in a period other than a backflow period in which the backflow of the fluid is detected, and (ii) to calculate the estimated fluid information on the basis of a corrected average frequency signal obtained by correcting the average frequency signal in the backflow period.

3. The fluid measuring apparatus according to claim 2, wherein the corrected average frequency signal is a signal obtained by multiplying the average frequency signal by a predetermined coefficient.

4. The fluid measuring apparatus according to claim 1, further comprising an analyzing device configured to output an average frequency signal based on the received light signal,
wherein said calculating device is configured to:
(i) calculate first fluid information based on the average frequency signal and second fluid information by correcting the first fluid information,
(ii) output the first fluid information as the estimated fluid information in a period other than a backflow period in which the backflow of the fluid is detected, and
(iii) output the second fluid information as the estimated fluid information in the backflow period.

5. The fluid measuring apparatus according to claim 4, wherein the second fluid information is information obtained by inverting a polarity of the first fluid information.

6. The fluid measuring apparatus according to claim 1, further comprising:
an average calculating device configured to average previously-estimated fluid information and to calculate average fluid information; and
a limiting device configured to limit a backflow period in which the backflow of the fluid is detected to be shorter as a flow volume or a flow velocity of the fluid indicated by the average fluid information increases.

7. The fluid measuring apparatus according to claim 1, wherein said light receiving device includes: a first light receiving element and a second light receiving element,
said detecting device is configured to detect the backflow of the fluid based on a first received light signal outputted from the first light receiving element, and
said calculating device is configured to calculate the estimated fluid information based on the detection result of said detecting device and a second received light signal outputted from the second light receiving element.

8. A fluid measuring apparatus comprising:
an irradiating device configured to irradiate a fluid with light;
a light receiving device configured to receive light scattered by the fluid;
a detecting device configured to detect a backflow of the fluid based on a received light signal of said light receiving device;
a calculating device configured to calculate estimated fluid information indicating a flow volume or a flow velocity of the fluid, based on a detection result of said detecting device and the received light signal of said light receiving device; and
an analyzing device configured to output an average frequency signal based on the received light signal,
wherein said calculating device is configured to (i) calculate the estimated fluid information based on the average frequency signal in a period other than a backflow period in which the backflow of the fluid is detected, and (ii) calculate the estimated fluid information based on a corrected average frequency signal obtained by correcting the average frequency signal in the backflow period.

9. A fluid measuring apparatus comprising:
an irradiating device configured to irradiate a fluid with light;
a light receiving device configured to receive light scattered by the fluid;
a detecting device configured to detect a backflow of the fluid based on a received light signal of said light receiving device;

a calculating device configured to calculate estimated fluid information indicating a flow volume or a flow velocity of the fluid, based on a detection result of said detecting device and the received light signal of said light receiving device; and an analyzing device configured to output an average frequency signal based on the received light signal, wherein said calculating device is configured to
  (i) calculate first fluid information based on the average frequency signal and second fluid information by correcting the first fluid information,
  (ii) output the first fluid information as the estimated fluid information in a period other than a backflow period in which the backflow of the fluid is detected, and
  (iii) output the second fluid information as the estimated fluid information in the backflow period.

10. A fluid measuring apparatus comprising:

an irradiating device configured to irradiate a fluid with light;

a light receiving device configured to receive light scattered by the fluid;

a detecting device configured to detect a backflow of the fluid based on a received light signal of said light receiving device;

a calculating device configured to calculate estimated fluid information indicating a flow volume or a flow velocity of the fluid, based on a detection result of said detecting device and the received light signal of said light receiving device;

an average calculating device configured to average previously-estimated fluid information and to calculate average fluid information; and a limiting device configured to limit a backflow period in which the backflow of the fluid is detected to be shorter as a flow volume or a flow velocity of the fluid indicated by the average fluid information increases.

11. A fluid measuring apparatus comprising:

an irradiating device configured to irradiate a fluid with light;

a light receiving device configured to receive light scattered by the fluid, the light receiving device includes a first light receiving element and a second light receiving element;

a detecting device configured to detect a backflow of the fluid based on a first received light signal outputted from the first light receiving element; and a calculating device configured to calculate estimated fluid information indicating a flow volume or a flow velocity of the fluid, based on a detection result of said detecting device and a second received light signal outputted from the second light receiving element.

* * * * *